United States Patent
Neshat

(10) Patent No.: US 8,523,569 B2
(45) Date of Patent: Sep. 3, 2013

(54) CONTROLLED RELEASE LOCAL ANESTHETIC FOR POST DENTAL SURGERY AND METHOD OF USE

(76) Inventor: Khashayar Kevin Neshat, Raleigh, NC (US)

(*) Notice: Subject to any disclaimer, the term of this patent is extended or adjusted under 35 U.S.C. 154(b) by 436 days.

(21) Appl. No.: 12/810,195

(22) PCT Filed: Dec. 22, 2008

(86) PCT No.: PCT/US2008/087952
§ 371 (c)(1),
(2), (4) Date: Jun. 23, 2010

(87) PCT Pub. No.: WO2009/086270
PCT Pub. Date: Jul. 9, 2009

(65) Prior Publication Data
US 2010/0280069 A1  Nov. 4, 2010

Related U.S. Application Data

(60) Provisional application No. 61/017,208, filed on Dec. 28, 2007.

(51) Int. Cl.
| A61K 31/47 | (2006.01) |
| A61K 31/445 | (2006.01) |
| A61K 31/381 | (2006.01) |
| A61K 31/167 | (2006.01) |
| A61K 31/245 | (2006.01) |
| A61P 23/02 | (2006.01) |

(52) U.S. Cl.
USPC .......... 433/215; 424/422; 424/423; 514/18.3; 514/312; 514/330; 514/818; 514/964

(58) Field of Classification Search
USPC .......................................................... 424/26
See application file for complete search history.

(56) References Cited

U.S. PATENT DOCUMENTS

| 4,293,593 A | 10/1981 | Yoldas |
| 4,622,219 A | 11/1986 | Haynes |
| 4,725,442 A | 2/1988 | Haynes |
| 4,919,939 A | 4/1990 | Baker |
| 4,938,763 A | 7/1990 | Dunn et al. |
| 5,061,492 A | 10/1991 | Okada et al. |
| 5,188,837 A | 2/1993 | Domb |
| 5,227,165 A | 7/1993 | Domb et al. |
| 5,618,563 A | 4/1997 | Berde et al. |
| 6,074,674 A | 6/2000 | Jay et al. |
| 6,143,353 A | 11/2000 | Oshlack et al. |
| 6,217,911 B1 | 4/2001 | Vaugn et al. |
| 6,426,339 B1 | 7/2002 | Berde et al. |
| 6,630,486 B1 | 10/2003 | Royer |
| 7,131,997 B2 | 11/2006 | Bourne et al. |
| 7,261,889 B2 | 8/2007 | Weber et al. |
| 2003/0152637 A1 | 8/2003 | Chasin et al. |
| 2003/0175357 A1 | 9/2003 | Goldenhim et al. |
| 2003/0185872 A1* | 10/2003 | Kochinke ............ 424/426 |
| 2005/0036955 A1* | 2/2005 | DeGould ............. 424/53 |

FOREIGN PATENT DOCUMENTS

| WO | 9405265 | 3/1994 |
| WO | 2007070228 A2 | 6/2007 |

OTHER PUBLICATIONS

Okawa et al., Anxiety May Enhance Pain during Dental Treatment, Bull Tokyo Dent. Coll., 2002, 46 (3), pp. 51-58.*
Greengrass, Tropical bupivacaine for pain control following simple dental extractions, British Dental Journal 1998, vol. 184, No. 7, pp. 354-355, http://www.nature.com/bdj/journal/v184/n7/abs/4809623a.html.
Bhowmik, Preparation and in vitro characterization of slow release testosterone nanocapsules in alginates, Acta Pharm. 56 (2006) 417-429.

* cited by examiner

*Primary Examiner* — Walter Webb
(74) *Attorney, Agent, or Firm* — James G. Passé; Passé Intellectual Property, LLC

(57) ABSTRACT

The present invention relates to a method of delivering local anesthetic after dental extraction surgery. The present invention relates to packing the tooth socket with a tinned release local anesthetic which is coordinated with an initial local anesthetic and which lasts up to 5 days. The socket can be surgically sealed or the implant can act as the sealing means.

3 Claims, No Drawings

CONTROLLED RELEASE LOCAL ANESTHETIC FOR POST DENTAL SURGERY AND METHOD OF USE

This application claims priority from U.S. provisional application No. 61/017,208 filed on Dec. 28, 2007 and incorporated herein in its entirety by reference.

COPYRIGHT NOTICE

A portion of the disclosure of this patent contains material that is subject to copyright protection. The copyright owner has no objection to the reproduction by anyone of the patent document or the patent disclosure as it appears in the Patent and Trademark Office patent files or records, but otherwise reserves all copyright rights whatsoever.

BACKGROUND OF THE INVENTION

1. Field of the Invention

The present invention relates to novel methods for treating post operative dental pain. The present invention also provides novel pharmaceutical formulations for delivery of local anesthetics for post operative dental pain. The specific invention relates to sustained released local anesthetics for implantation into a dental socket or space post-operatively.

2. Description of Related Art

Local anesthetics are designed to block the conduction and generation of the sense of pain by increasing the perceived threshold for excitation in the corresponding nerve that transmits the sensation. It accomplishes this by slowing down the propagation of an impulse through the nerve and by reducing the rate of rise of the action potential of the nerve. Local anesthetics are considered very potent and their use usually results in complete loss of the sensation of feeling in the area to which a local anesthetic is administered. The sensations that local anesthetics block include pain, temperatures sensation, touch, proprioception, and skeletal muscle tone.

Some of the commonly used local anesthetics include mepivicaine, xylocalne and bupivicaine. These local anesthetics are of medium duration with half lives somewhere in the about 2 to 3 hour range with effects lasting out to as long as about 20 hours. Frequently the local anesthetics are mixed with epinephrine a potent vasoconstrictor. Epinephrine reduces the clearance of the local anesthetic thus extending the effective time of action even further. This action is ideal for dental type surgery, for example during tooth extraction. Local anesthetics are preferred over general anesthetics in localized dental surgery because of the complications that can occur with general anesthesia. Even when general anesthetics are used in dental surgery, a local anesthetic is still used along with the general anesthetic to insure a reduction in pain as the general anesthetic wears off.

The local anesthetics are designed to remain active during dental surgery and beyond that for pain moderation. Severe pain in most people lasts somewhere around 1 to 3 days after dental surgery and typically a centrally acting narcotic is given such as meperidine, oxysodone, hydrocodone, or codeine to mitigate pain during this time period. The opiate drugs act through the opiate receptors in the central nervous system and are usually orally self-medicated after dental surgery. It is also typical that a prescription is given for these opiate medications and by the time the patient fills the prescription, takes the oral medication and it begins to work, the local anesthetic has begun to wear off sufficiently that there is not an adverse additive effect. Although centrally acting narcotics are very effective in the treatment of post surgical dental pain, they are associated with serious side effects, including nausea and vomiting, addiction, respiratory depression, apnea, circulatory depression, respiratory arrest, shock and cardiac arrest.

Post dental surgery administration of additional local anesthetics would be preferable. However, the ability to administer additional local anesthetics is beyond the skills of the average patient. Furthermore, the additive effects of overlapping dosages if anesthetic administration is not timed properly can create risks that make patient self-dosing unacceptable. Even further, since access to the socket cavity is achieved right after tooth extraction before the initial local anesthetic has begun to wear off, timing the administration in the socket at that time during the procedure with current products can also lead to a dangerous additive effect.

The administration of local anesthetics with a long duration has been used to reduce the number of times a local needs to be administered. A number of different approaches have been attempted to extend the life of the local anesthetics. Approaches have included the addition of epinephrine added to the local anesthetic mentioned above as well as long acting or sustained released injectables formulations of a local anesthetic. While these products could be dosed after surgery as well they do not take into consideration the pre-surgical doses and their rapid onset creates a substantial risk of overdose. Sustained release carriers for injectable local anesthetics have been described. For example, U.S. Pat. Nos. 4,725,442 and 4,622,219 (Haynes) are directed to methoxyflurane-containing microdroplets coated with a phospholipid prepared by sonication, which are suitable for intradermal or intravenous injection into a patient for inducing local anesthesia. Such microdroplets are said to cause long-term local anesthesia when injected intradermally, giving a duration of anesthesia considerably longer than the longest acting conventional local anesthetic (bupivacaine).

U.S. Pat. No. 5,188,837 (Domb) relates to a microsuspension system containing liposheres having a layer of a phospholipid imbedded on their surface. The core of the liposphere is a solid substance to be delivered, or the substance to be delivered is dispersed in an inert vehicle. The substance to be delivered can be, e.g., nonsteroidal anti-inflammatory compounds, local anesthetics, water insoluble chemotherapeutic agents and steroids.

Other formulations directed to injectable microcapsules, etc. are known. For example, U.S. Pat. No. 5,061,492 describes prolonged release microcapsules of a water-soluble drug in a biodegradable polymer matrix which is composed of a copolymer of glycolic acid and a lactic acid. The microcapsules are prepared as an injectable preparation in a pharmaceutically acceptable vehicle. The particles of water soluble drug are retained in a drug-retaining substance dispersed in a matrix of the lactic/glycolic acid copolymer in a ratio of 100/1 to 50/50 and an average molecular weight of 5,000-200,000. The injectable preparation is made by preparing a water-in-oil emulsion of an aqueous layer of drug and drug retaining substance and an oil layer of the polymer, thickening and then water-drying.

U.S. Pat. No. 4,938,763 (Dunn, et al.) is related to a biodegradable polymer for use in providing syringe able, in-situ forming, solid biodegradable implants for animals. In one aspect of this reference, a thermosetting system is utilized which utilizes copolymers which may be derived from polylactides and/or polyglycolides, combinations and mixtures of these and other polymers.

U.S. Pat. No. 4,293,539 (Ludwig, et al.) is directed to controlled release formulations comprised of a microbial agent dispersed throughout a copolymer derived from lactic acid and glycolic acid. The copolymer is derived from 60-95% lactic acid and 40-5% glycolic acid by weight, and has a molecular weight of 6,000-35,000. An effective amount of the copolymeric formulation is administered by subcutaneous or intramuscular administration.

WO 94/05265 describes improved biodegradable sustained release systems consisting of a polymeric matrix incorporating a local anesthetic for the prolonged administration of the local anesthetic agent. The devices are selected on the basis of their degradation profiles: release of the topical anesthetic in a linear, controlled manner over the period of preferably two weeks and degradation in vivo with a half-life of less than six months, more preferably two weeks, to avoid localized inflammation. Tile disclosure states that all anti-inflammatory can be incorporated into the polymer with the local anesthetic to reduce encapsulation for optimal access of drug to its site of action. The anti-inflammatories that are said to be useful include steroids such as dexamethasone, cortisone, prednisone, and others routinely administered orally or by injection.

It would accordingly be useful to have a composition and method that allows the use of local anesthetics in dental surgery especially tooth extraction without the need to use opiates or to risk overdosing the patient.

SUMMARY OF THE INVENTION

The present invention relates to both a method and compositions for the treatment of dental pain post surgically. The present invention relates to timed released local anesthetic compositions which are positioned in the open dental cavity after tooth extraction and begin releasing anesthetic in coordination with the pre-operative local anesthetics that are given and maintain a release for a period of between about 4 hours and about 5 days post surgically.

Accordingly, in one embodiment of the invention there is a solid controlled release pharmaceutical formulation of a dental local anesthetic formulated of a size and shape that is capable of being placed in a tooth extraction cavity and formulated to release anesthetic in coordination with a prior administered dental local anesthetic and lasting between about 4 hours and about 5 days post surgically.

In another embodiment of the present invention there is a method of administering local anesthetics during a tooth extraction comprising:
a) injecting a first dental local anesthetic in the area surrounding a tooth to be extracted;
b) extracting the tooth to produce an extraction cavity; and
c) placing a solid controlled release pharmaceutical formulation of a second dental local anesthetic in the extraction cavity, the formulation sized and shaped to fit the extraction cavity and formulated to begin releasing the second anesthetic in coordination with the first anesthetic such that it begins releasing as the first anesthetic is wearing off.

The present invention also relates to a kit of for the delivery of pain relief in a selected patient during tooth extraction comprising an injectable first local anesthetic and a second local anesthetic formulated of a size and shape to fit in an extraction cavity and formulated to begin releasing the second anesthetic in coordination with the first anesthetic as the first local anesthetic is wearing off.

These and other objects of the present invention will be clear when taken in view of the detailed specification.

DETAILED DESCRIPTION OF THE INVENTION

Prior to the present invention there has been no formulation or method for treating pain after dental tooth extraction surgery with local anesthetics other than by injection. This is despite the long term availability of local anesthetics and some forms of sustained release pain relievers. Dentists have relied on patient self medication and on narcotics. The present invention discovers that a solid sustained release local anesthetic that fits into the tooth extraction site and coordinates its initial release with the tapering off of a first injected local anesthetic solves the problems of the prior art.

While this invention is susceptible of embodiment in many different forms, there is shown in the drawings and will herein be described in detail specific embodiments, with the understanding that the present disclosure of such embodiments is to be considered as an example of the principles and not intended to limit the invention to the specific embodiments shown and described. In the description below, like reference numerals are used to describe the same, similar or corresponding parts in the several views of the drawings. This detailed description defines the meaning of the terms used herein and specifically describes embodiments in order for those skilled in the art to practice the invention.

The terms "a" or "an", as used herein, are defined as one as or more than one. The term "plurality", as used herein, is defined as two or more than two. The term "another", as used herein, is defined as at least a second or more. The terms "including" and/or "having", as used herein, are defined as comprising (i.e., open language). The term "coupled", as used herein, is defined as connected, although not necessarily directly, and not necessarily mechanically.

Reference throughout this document to "one embodiment", "certain embodiments", and "an embodiment" or similar terms means that a particular feature, structure, or characteristic described in connection with the embodiment is included in at least one embodiment of the present invention. Thus, the appearances of such phrases or in various places throughout this specification are not necessarily all referring to the same embodiment. Furthermore, the particular features, structures, or characteristics may be combined in any suitable manner in one or more embodiments without limitation.

The term "or" as used herein is to be interpreted as an inclusive or meaning any one or any combination. Therefore, "A, B or C" means any of the following: "A; B; C; A and B; A and C; B and C; A, B and C". An exception to this definition will occur only when a combination of elements, functions, steps or acts are in some way inherently mutually exclusive.

As used herein, dental "local anesthetics" refers to those local anesthetics which can be used during oral/dental surgery for the extraction of teeth. Typically, they are injected but in the present invention they are reformulated for sustained release and work in a topical manner. Local anesthetics (both first and second local anesthetics as used herein and being the same or different) include bupivacaine, mepivicaine, articaine, ropivacaine, dibucaine, etidocaine, tetracaine, lidocaine, xylocalne, and the like including mixtures and/or salts and/or derivatives thereof. The first dental local anesthetic of the present invention is the injectable version of these local anesthetics. The second is a solid sustained release formulation. These local anesthetics have a variable half life and duration and are selected based on their various properties and compatibility with the particular patient and second anesthetic matched with the properties of the first local anesthetic.

For example, a relatively long-acting local anesthetic, bupivacaine hydrochloride, is commercially available as Marcaine®. Hydrochloride in sterile isotonic solutions with and without epinephrine (as bitartrate) 1:200,000 for injection via local infiltration, peripheral nerve block, and caudal and lumbar epidural blocks. After injection of Marcaine for caudal, epidural or peripheral nerve block in man, peak levels of bupivacaine in the blood begin to decline after about 1 hour, followed by a decline to insignificant levels during, the next three to six hours.

The surgical removal of a tooth, i.e. tooth extraction, is accomplished by prior administration of local anesthetics often accompanied with general anesthesia in an oral surgery case. A local anesthetic or mixture of local anesthetics with or without an augmenting agent is administered by injection as an infiltration or a nerve block for the extraction of a tooth. A combination of incisions, tissue reflections, elevation of teeth, sectioning of teeth with a drill or hand instrument, removal of surrounding alveolar bone, and pressure extraction with forceps normally is successful in removing a desired tooth. The remaining open tooth socket or extraction cavity is normally cleaned and at times sutured and gauze placed over the site for approximately one hour to aid in cessation of post-surgical bleeding. In some cases the surgical site is left unsutured with only the inserted anesthetic of the present invention to close the surgical site. The surgery itself takes approximately 30-60 minutes from the time of injection of local anesthetic to the extraction of a tooth. It is at this point in the tooth extraction that the present invention would be administered i.e. about 30 to 60 minutes after administration of the first local anesthetic.

As used herein, the terms, "controlled release pharmaceutical formulation" and "sustained release" indicate a prolongation of the onset of release and a prolongation of the duration of release and/or duration of action of an active agent and are intended to be interchangeable, unless otherwise indicated.

Sustained release materials for achieving a controlled release include release materials such as controlled release polymer materials. Polymers could include polyanhydrides, copolymers of acid and glycolic acid, poly(lactic) acid, poly (glycolic) acid, polyesters, polyorthoesters, proteins, polysaccharides and/or combinations thereof. They are clearly not limited to these materials. Preferably, the polymers are biodegradable so that manual removal from the extraction cavity is avoided. Further, the materials must be biocompatible and compatible with local anesthetics. The solid controlled release pharmaceutical formulation contains a "second" dental local anesthetic. This can be the same local anesthetic as used in the first local anesthetic or a different one or a mixture or the like. This second local anesthetic will be formulated however for controlled release in order to have a localized topical anesthetic effect. Accordingly, the formulation will be a solid dosage form such and a tablet, gel or moldable solid. The size and shape will be such that the dentist or other technician can place the formulation inside the extraction cavity. Accordingly, in one embodiment the formulation is malleable, that is can be shaped like clay or putty so that the bolus can be placed in the cavity and conform to the surrounding tissue without leaving a pocket. In another embodiment the formulation is formed to fill the cavity sufficiently that surgical suturing is not needed and the bolus of local anesthetic becomes the closure means for the cavity. In this embodiment the local anesthetic could be formulated into a gel or other pliable surgically acceptable material for that purpose.

The controlled release aspect of the present invention is particularly critical. Since there is already going to be a local anesthetic in the locality of the extraction cavity, application of additional local anesthetic could be toxic. Coordination of the onset of the second anesthetic with the release of the first anesthetic is necessary. Accordingly, one aspect of the present formulation is that the timing on the onset or release and rate of release of the second local anesthetic is coordinated with the decline in levels of the first local anesthetic. So for example where the bolus is deposited in the extraction cavity after one hour and the first local anesthetic begins to decline after 2 hours and declines to insignificant levels over 6 hours, the present invention would be formulated to begin release after about one hour after insertion and not release the full dosage, but rather taper in the dosage over the first 5 hours. Thus, after 6 hours the peak levels of anesthetic will have been reached as the first anesthetic has worn off. According, it is clear that the formulation must be made to be coordinated with a prior administered dental local anesthetic and not just formulated in a one formulation fits all manner or a manner that would be consistant with the second local anesthetic being the only local that is administered. In another embodiment the anesthetic of the present invention is fixed to release at a given time that coordinates with the first given anesthetic. So for example a product that began release at 1, 2, 3, 4 or 5 hours could be used with the initially injected local anesthetics exampled herein. That way a single product could be provided while still coordinating the onset of effect of the present invention with the first injected anesthetic. The coordination of this invention as necessary could be such that there is some overlap as desired or in another embodiment the onset of the second could wait until the first has worn off. One skilled in the art in view of this disclosure could determine the exact best way to coordinate the onset of the second local anesthetic in view of this disclosure and the first given anesthetic.

Tooth extraction while serious surgery, does not require prolonged analgesia. Accordingly, while the sustained effect needs to begin in a delayed manner the resulting effect needs to only be for up to about 5 days duration. In one embodiment the effect lasts as long as about 1 day, 2 days 3 days 4 days or 5 days. In another embodiment the second administered local anesthetic has a duration of less than about 1 day. The present invention in other embodiments begins its effect at about 1, 2, 3, 4 or 5 hours.

As used herein by the phrase "sized and shaped to fit the extraction cavity" is meant that the present invention dosages designed to fit in the open socket of the jaw after tooth extraction. This can be achieved by producing the controlled release formulation of a standard size that would fit into most tooth cavities. It could also be formulated in a number of sizes so that children, men, women and very large people would all have one that is sized to the needs of the surgeon. In one embodiment the formulation is malleable so that the surgeon can change the shape of the formulation to fit the particular cavity or such that upon inserting the formulation into the cavity it conforms its shape to the surrounding cavity. It can also be shaped so that it conforms completely to the cavity sufficiently to seal the cavity and lessen or eliminate the need for suturing the site after tooth removal.

The formulation of the present invention will then be designed to release local anesthetic into the cavity and thus be distributed to the surrounding area for the time periods indicated above. Where the formulation of the present invention is produced, of a material that decomposes within the cavity over time no further removal of the formulation is necessary. One skilled in the art can so formulate the present invention as desired.

As used herein, the term "patient" broadly refers to any animal that is to be treated with the compositions and by the methods herein disclosed. The disclosed sustained release formulation and methods for extraction cavity administration can provide prolonged and effective administration of local anesthetics. In particular, the product and method for extraction cavity administration of extended duration local anesthetic dosage forms according to the invention can provide localized pain blockade to any animal, e.g., any vertebrate, which it is desired to so anesthetize. In a preferred embodiment, the term "patient" includes humans in need of or desiring prolonged treatments, such as for treatment of pain immediately following dental surgery for tooth extraction.

Additional pharmaceutically active agents that can be incorporated into the present invention formulation of local anesthetics for extraction site administration, include, e.g., antibiotics such as sulfisoxazole, penicillin G, ampicillin, cephalosporinis, amikacin, gentamicin, tetracyclines, chloramphenicol, erythromycin, clindamycin, isoniazid, rifampin, and derivatives, salts and mixtures thereof; antifungals such as amphotericin B, nystatin, ketoconazole; antivirals such as acyclovir, amantadine, chlorahexidine; and other art known anti-infective.

Augmenting agents can also be included in formulations according to the present invention. They are compositions or compounds that prolong the duration of local anesthesia and/or enhance the effectiveness of local anesthetic agents when delivered to the site of local anesthetic administration.

In certain embodiments of the invention, the augmenting agent can be from one or more of the following general types or classes of agents, including glucocorticosteroid agents, alkalinizing agents, non-glucocorticoid steroids such as, e.g., neuroactive steroids and/or steroid or nonsteroid modulators of gamma amino butyric acid ("GABA") receptors, modulators of ionic transport across cell membranes, including, e.g., modulators of membrane transport of monovalent and divalent metal ions such as, for example, blockers or enhancers of sodium, potassium and/or calcium transport across cell membranes, antipyretic agents, adrenergic receptor agonists or antagonists, such. as .alpha.2 receptor agonists, tubulin binding agents, including, e.g., agents that are capable of either causing formation or disruption of intracellular microtubules, osmotic polysaccharides, agonists and antagonists of potassium ATP channels, i.e., able to open or close potassium ATP channels, Na, K-ATPase inhibitors and enhancers, neurokinin antagonists, PLC (i.e., phosphatidylinositol-specific phospholipase C) inhibitors, inhibitors of leukocyte glucose metabolism and anti-convulsants. The augmenting agent can also be an analeptic, a tranquilizing agent, an ataretic, an antidepressant, an anti-seizure agent, leukotriene and prostaglandin agonists and inhibitors, phosphodiesterase agonists and inhibitors, e.g., based on cAMP, and combinations of any of the foregoing. Vasoconstrictive agents provided in controlled release form also provide for unexpected and surprising augmentation of duration and potency of local anesthetics relative to immediate release forms of vasonstrictive agents heretofore known to the art. The aforementioned types of augmenting agents may be used alone or in any mixture or combination of each such agent to provide effective augmentation of local anesthesia where desired.

Augmenting agents that are vasoconstrictor agents in sustained release form include, but are not limited to, catecholamines e.g., epinephrine, norepinephrine and dopamine as well as, e.g., metaraminol, phenylephrine, methoxamine, mephentermine, methysergide, ergotamine, ergotoxine, dihydroergotamine, sumatriptan and analogs, and alpha-1 and alpha-2 adrenergic agonists, such as, e.g., clonidine, guanfacine, guanabenz and dopa (i.e., dihydroxyphenylalanine), methyldopa, ephedrine, amphetamine, methamphetamine, methylphenidate, ethylnorepinephrine ritalin, pemoline and other sympathomimetic agents, including, active metabolites, derivatives and mixtures of any of the foregoing.

Surprisingly, locally acting vasoconstrictive agents also provide effective augmentation of local anesthesia that is unexpectedly superior to that provided by immediate release vasoconstrictive agents. While not wishing to be bound by any hypothesis as to how vasoconstrictive agents in sustained release form might greatly prolong local-anesthetic activity, it is believed that sustained release vasoconstrictor agents provide a controlled and nontoxic vasoconstrictor activity that reduces the rate of local anesthetic washout from the treated tissue area to prolong the presence of effective concentrations of local anesthetic in the tissue. It is known to the art that vasoconstrictors, e.g., epinephrine, prolong local anesthetic activity for, at best, about 1 hour and that if excessive amounts of epinephrine or other vasoconstrictor is administered in an attempt to further prolong local anesthesia, local circulation may be so disrupted as to cause tissue necrosis and gangrene.

Any pharmaceutically acceptable vehicle or formulation suitable for local infiltration into a site to be anesthetized, that is able to provide a sustained release of an active agent may be employed to provide for prolonged local anesthesia as needed. Slow release formulations known in the art include specially coated pellets, polymer formulations or matrices for surgical insertion or as sustained release microparticles, e.g., microspheres or microcapsules, for implantation, insertion or injection, wherein the slow release of the active medicament is brought about through sustained or controlled diffusion out of the matrix and/or selective breakdown of the coating of the preparation or selective breakdown of a polymer matrix. Other formulations or vehicles for sustained or immediate delivery of an agent to a preferred localized site in a patient include, e.g., suspensions, emulsions, liposomes and any other suitable, art known, delivery vehicle or formulation.

EXAMPLES

Example 1

Preparation of Sustained Release Local Anesthetic

A one day supply of bupivacaine is formulated into a sustained release matrix. Optionally it is also formulated with a 1:100,000 ratio of epinephrine as an augmenting agent. The matrix is designed to begin releasing medication after one hour and reach a peak release at about 3 hours. The matrix is shaped into a pellet the size of a tooth extraction cavity of a malleable material and of material that will decompose over a period of time.

Example 2

Preparation of Sustained Release Local Anesthetic

A one day supply of bupivacaine is formulated into a sustained release matrix. Optionally, it is also formulated with a 1:100,000 ratio of epinephrine as an augmenting agent. The matrix is designed to begin releasing after about 6 hours time and to reach a peak release at about 9 hours time. The matrix is shaped into a pellet the size of a tooth extraction cavity of a malleable material and of a material that will decompose over a period of time.

Example 3

Tooth Extraction and Administration Method

A patient is prepared for surgical extraction of a tooth. Injectable lidocaine 2% with 1:100,000 epinephrine is injected the area around the tooth sufficient for local anesthesia. The injectable local anesthetic is administered in the way of a block in the mandible and infiltrations in the maxilla. A number 15 blade is utilized to make an incision in a sulcular fashion around the tooth. An incision is made in a hockey stick fashion lateral to the ridge at al times to avoid the lingual nerve. Sub-periosteal dissection is done with a periosteal elevator. Elevation is then accomplished with dental elevators and extraction of the tooth is done with appropriate forceps. The surgical extraction cavity is curetted gently and irrigated copiously with NS solution. A pellet of the formulation in Example 1 is positioned in the extraction cavity and then gently massaged to cause it to conform to the cavity dimensions. Gauze is placed in the extraction site area and the patient is instructed to bite on the gauze gently for 1 hour.

Example 4

Tooth Extraction and Administration Method

A patient is prepared for surgical extraction of a tooth. Injectable bupivacaine 0.5% with 1:100,000 epinephrine is injected the area around the tooth sufficient for local anesthesia. The injectable local anesthetic is administered in the way of a block in the mandible and infiltrations in the maxilla. A number 15 blade is utilized to make an incision in a sulcular fashion around the tooth. An incision is made in a hockey stick fashion lateral to the ridge at al times to avoid the lingual nerve. Sub-periosteal dissection is done with a periosteal elevator. Elevation is then accomplished with dental elevators and extraction of the tooth is done with appropriate forceps. The surgical extraction cavity is curetted gently and irrigated copiously with NS solution. A pellet of the formulation in Example 2 is positioned in the extraction cavity and then gently massaged to cause it to conform to the cavity dimensions. Gauze is placed in the extraction site area and the patient is instructed to bite on the gauze gently for 1 hour.

Example 5

Combination Administration

A tooth extraction is done according to claim 4 except both lidocaine as in example 3 and bupivacaine as in example 4 are uses as the injectable local anesthetic. Once again the pellet described in Example 2 is utilized as the post operative local anesthetic.

What is claimed is:

1. A method of administering local anesthetics for controlling pain during and after a tooth extraction comprising:
    a) injecting a first dental local anesthetic in the tissue surrounding a tooth to be extracted;
    b) extracting the tooth to produce an extraction cavity; and
    c) placing a solid controlled release pharmaceutical formulation of a second dental local anesthetic in the extraction cavity; the formulation sized and shaped to fit the extraction cavity, wherein the formulation doses the extraction cavity and is formulated to begin releasing the second anesthetic in coordination with the first anesthetic such that it begins releasing the second anesthetic as the first anesthetic is wearing off to lower the risk of an overdose of anesthetic.

2. A method according to claim 1 wherein the second anesthetic is selected from the group comprising bupivacaine, mepivicaine, articaine, ropivacaine, dibucaine, etidocaine, tetracaine, lidocaine and xylocaine.

3. A method of administering local anesthetics during and after a tooth extraction comprising:
    a) injecting a first dental local anesthetic in the tissue surrounding a tooth to be extracted;
    b) extracting the tooth to produce an extraction cavity; and
    c) placing a solid controlled release pharmaceutical formulation of a second dental local anesthetic in the extraction cavity; the formulation sized and shaped to fit the extraction cavity, wherein the formulation is sutured within the cavity and formulated to begin releasing the second anesthetic in coordination with the first anesthetic such that it begins releasing the second anesthetic as the first anesthetic is wearing off to reduce the risk of an overdose of anesthetic.

* * * * *